United States Patent [19]

Cashion

[11] 4,379,843

[45] Apr. 12, 1983

[54] IMMOBILIZATION OF POLYNUCLEOTIDES AND POLYPEPTIDES WITH TRITYLATED POLYSACCHARIDES

[76] Inventor: Peter Cashion, 821 Hanson St., Fredericton, New Brunswick, Canada, E3B 4A6

[21] Appl. No.: 228,258

[22] Filed: Jan. 26, 1981

[51] Int. Cl.$^3$ .............. C12N 11/10; C12P 19/34; C12N 11/12; C12N 11/06
[52] U.S. Cl. ...................... 435/178; 435/91; 435/179; 435/181; 435/814; 435/815
[58] Field of Search .............. 435/174, 177, 178, 179, 435/181, 89, 90, 91, 814, 815

[56] References Cited

U.S. PATENT DOCUMENTS

| | | | |
|---|---|---|---|
| 3,278,392 | 10/1966 | Patchornik et al. | 195/63 |
| 3,647,630 | 3/1972 | Franks | 195/63 R |
| 3,833,555 | 9/1974 | Keys et al. | 260/209 R |
| 3,841,969 | 10/1974 | Emery et al. | 195/63 |
| 3,909,360 | 9/1975 | Horiuchi et al. | 195/68 |
| 3,914,183 | 10/1975 | Johansson et al. | 252/184 |
| 3,947,352 | 3/1976 | Cuatrecasas et al. | 210/31 |
| 4,006,059 | 2/1977 | Butler | 195/63 X |
| 4,038,140 | 7/1977 | Jaworek et al. | 195/63 |
| 4,090,919 | 5/1978 | Chibata et al. | 195/63 |
| 4,167,446 | 9/1979 | Huper | 435/45 |

OTHER PUBLICATIONS

Walden K. Roberts, "Use of Benzoylated Cellulose Columns for the Isolation of Poly(adenylic Acid) Containing RNA and Other Polynucleotides with Little Secondary Structure", Biochemistry, vol. 13, No. 18, 1974, pp. 3677-3682.

Peter Cashion et al., "Hydrophobic Affinity Chromatography of Nucleic Acids and Proteins", *Nucleic Acids Research*, vol. 8, No. 5, Mar. 11, 1980, pp. 1167-1185.

Peter Cashion et al., "Hydrophobic Affinity Chromatography of Nucleic Acids and Proteins, II, Activity of Tritylsepharose Immobilized Enzymes", *Nucleic Acids Research*, Symposium Series, No. 7, May 1980, pp. 173-189.

*Primary Examiner*—David M. Naff
*Attorney, Agent, or Firm*—Barnes & Thornburg

[57] ABSTRACT

Polynucleotides and Polypeptides are immobilized and/or isolated by using a triphenylmethyl ether derivative of polysaccharides in hydrated form.

40 Claims, No Drawings

IMMOBILIZATION OF POLYNUCLEOTIDES AND POLYPEPTIDES WITH TRITYLATED POLYSACCHARIDES

BACKGROUND OF THE INVENTION

This invention relates to a composition and a method for isolating or immobilizing polynucleotides and polypeptides by means of aromatic derivatives of certain carbohydrates and, in particular, triphenylmethyl ether derivatives of polysaccharides.

The employment of a variety of support materials to attract and strongly bond substances such as nucleic acids and proteins has advanced research endeavors in the field of biological chemistry. The physical/chemical forces between such substances and supports is generally attributable, either exclusively or in combination, to such mechanisms as covalent attachment, ionic bonding, hydrogen bonding, hydrophobic bonding, adsorption, and physical entrapment.

Special support materials are used to isolate and purify polynucleotides such as RNA or DNA for research purposes. In this regard, for example, isolation of poly A-containing mRNA and denatured DNA are currently very important manipulative procedures in biochemistry/molecular biology. Furthermore in the field of biocatalysts, proteins in the form of specific enzymes are joined to, and sometimes stabilized by, support materials. Such activated materials are now gaining favorable commercial acceptance. As is generally known, there are several advantages accruing from the binding of enzymes to suitable supports:

(1) Given a reasonable stability of the immobilized enzyme, one can reuse the enzyme a number of times with considerable saving of time and money;

(2) Ease and speed of separating the products of a given reaction from the immobilized enzymatic catalysts; and (3) Replacing routine chemical synthetic methods with enzyme-mediated reactions, as in the synthesis of penicillin derivatives, with attendant improvements in the yield, speed, and stereochemical purity.

The particular type of chemical linkage, covalent or non-covalent, joining the enzyme to the support may conveniently be used to categorize and distinguish between the various types of enzyme immobilization/-stablization methods. Generally speaking, enzymes may be immobilized to solid matrices by means of non-covalent or covalent chemical bonds. In the case of non-covalent bonds, conditions being very mild and uncomplicated, the ultimate enzyme attachment yields may be quite high; furthermore, little time or skill is required. One general drawback of this approach is that, for a given enzyme, conditions optimal for catalytic efficiency may not coincide with conditions optimal for irreversible immobilization of the enzyme to the support, and as a result, leakage may ensue. In the case of covalent bonds linking an enzyme with its solid support, the chemical requirements to effect this linkage may be excessively harsh, as far as pH, salt, or organic solvent requirements are concerned, so as to seriously denature or inactivate many fragile enzymes. Covalent bonds once established between an enzyme and support are stable, although recent investigators find unexpected instability for some apparently widely used covalent attachment methods. Given the nature of the chemistry employed, considerable skill is required to do these reactions well. For the reason just mentioned, covalent attachment methods, while adequate with some enzymes, have their limitations and often fail to provide a very broad-based generalized method of enzyme immobilization.

With regard to covalent methods of attaching enzymes to support materials, one general approach advocated by workers in the field involves the formation of amide or related bonds between certain amino groups of the enzyme and some activated form of the support involving azide, isocyanate, carbodiimides, or iminocarbonates. A further approach has been methods involving the use of diazo coupling agents. In this regard, U.S. Pat. No. 3,647,630 to Franks discloses a preparation of a diazotized anthranilate ester of cellulose. Another procedure uses Schiff's base techniques. U.S. Pat. No. 3,947,352 to Cuatrecasas et al. discloses affinity chromatographic techniques using intermediate Schiff bases formed from sodium metaperiodate with polysaccharides. Another class of reagents found useful are the halides and sulfates of titanium, tin, zirconium, or iron derivatives of polysaccharides as set forth in U.S. Pat. No. 3,841,969 to Emery et al. In this general category also are the various cyanogen halide activated polysaccharides as disclosed in U.S. Pat. Nos. 3,914,183 to Johansson et al. and 4,167,446 to Huper. Furthermore, substantial research has been conducted with respect to ester types of linkages with polysaccharides and their derivatives to achieve activation thereof. In this regard, U.S. Pat. No. 3,909,360 to Horiuchi et al. discloses water-insoluble carrier-bound enzymes, formed by the use of fatty acid esters of polysaccharides. U.S. Pat. No. 3,833,555 to Keys et al. discloses a polysaccharide cyclic carbonate containing compounds, the compositions being useful for insolubilizing enzymes. A further process for binding biologically active proteins in an aqueous phase is disclosed in U.S. Pat. No. 4,038,140 to Jaworek et al., wherein the use of activated polysaccharides is described having a hydrophilic graft co-polymer grafted thereinto. Further, U.S. Pat. No. 3,278,392 to Patchornik discloses the use of bromacetyl cellulose having bonded thereto enzymes through sulphhydryl groups or amino groups of the enzymes.

With regard to non-covalent chemical attachment methods, simple adsorption of a given enzyme to some solid support is occasionally employed. In practice, this approach may be very limited in that any changing of the reaction conditions for the adsorbed enzyme can have a rather unpredictable and often weakening effect on the relative tightness of the adsorption. Adsorption of some enzymes onto ion-exhange columns such as diethyl aminoethyl cellulose is occasionally used in laboratory work. The efficacy of this approach depends on a somewhat fortuitous situation in that at a given pH where an enzyme is maximally active, the celulose derivative must possess a rather high net positive charge. Water-insoluble aromatic tannin preparations are disclosed by Chibata et al. in U.S. Pat. No. 4,090,919; in this instance, enzymes are apparently immobilized through a combination of ionic and hydrophobic bonds, U.S. Pat. No. 4,006,059 to Butler discloses a hydrophobic non-covalent binding of proteins to support materials. Various hydrophilic solid supports such as cellulose or glass have been esterified with phenoxyacetyl groups beginning with the corresponding acid chlorides. Finally, benzoylated cellulose substrates have been used for the isolation of poly adenylic acid containing RNA and other polynucleotides, its use being described in the open literature, Biochemistry, Vol. 13, No. 18, pp. 3677–3682, 1974.

SUMMARY OF THE INVENTION

The present invention relates to a substantially simple, inexpensive, and facile procedure to achieve an effective support material that has a wide spectrum of affinities for polynucleotides and polypeptides. It has been found that tritylated polysaccharides are very useful in the affinity chromatography of nucleic acids and in the immobilization/stabilization of enzymes. This has been reported elsewhere in the literature: Cashion et al., Nucleic Acids Research 8, 1167–1185 (Mar. 11, 1980) and Cashion et al., Nucleic Acids Research, Symposium Series No. 7, pp. 173–189, May 1980. The present invention is to provide the art with a desideratum hitherto unsupplied; namely, a very versatile support, operating exclusively on non-covalent hydrophobic forces, wherein a variety of biologically important polynucleotide and polypeptide species may be isolated and purified; likewise, this tritylated support is the essential component in a generalized methodology whereby enzymes may be immobilized and stabilized for considerable periods of time. In general, the active group of this invention is a triphenylmethyl-(trityl-) ether derivative of polysaccharides. The ether bond formed in the aforementioned derivative is extremely stable in contrast to other prior methods for the isolation of poly A+ mRNA using poly U Sepharose, benzoylated cellulose, or covalent protein-immobilization techniques using CNBr. The use of these derivatives of polysaccharides also offers advantages over dT cellulose and poly U Sepharose methods for isolating poly A+ mRNA because of (1) higher binding capacity; (2) absolute resistance to contaminating nucleases, hence the half-life of the support is increased; and (3) an improved binding specificity with regard to the length of the poly A component of poly A+ mRNA.

It is therefore an object of this invention to provide a method for preparing an activated derivatized polysaccharide that has an effective hydrophobic affinity for polynucleotides and polypeptides.

It is another object of this invention to provide a stable enzymatic support body useful in research and commercial facilities.

It is another object of this invention to provide a novel hydrophobic affinity chromatographic method whereby proteins may be purified.

It is yet another object of this invention to provide a method of isolating and purifying polynucleotides in general, employing specific tritylated oligonucleotides, anchored hydrophobially to tritylated supports, whose primary sequences are complementary in a hydrogen bonding sense to sequences within the target polynucleotide.

It is still another object of this invention to provide a process for the isolating of poly A+ mRNA species.

It is still another main object of this invention to provide a novel immobilized enzyme matrix which allows a maximum degree of enzymatic activity for a long period of time and at the same time allows reuse thereof.

The attainment of one or more of the above objects of this invention is accomplished by forming a reaction product of the triphenylmethyl ether of polysaccharides, hydrating said reaction product, and thereafter contacting said hydrated reaction product with the polypeptide or polynucleotide.

DESCRIPTION OF THE INVENTION

In the compositions of this invention, polypeptides and polynucleotides are attracted to or bound together non-covalent hydrophobic bonds to the triphenylmethyl ether group which in turn is bonded covalently to a polysaccharide. It is postulated, but the invention is not to be assumed restricted thereby, that the triphenylmethyl ether derivative acts via hydrophobic bonding to the polynucleotides or polypeptides. Regarding the polynucleotides, the high specificity for poly A tracts which these triphenylmethyl derivatives exhibit is thought to arise from the more unstacked and hence accessible structure of this polypurine's bases. This is also believed to be the binding mechanism for denatured DNA. Likewise, the binding of polypeptides to such derivatives is thought to be attributable to accessible domains of hydrophobic amino acids on their surfaces. The sensitivity of such binding to detergents, organic solvents, salt concentrations, pH, and temperature supports this theory.

In its broader aspects, the subject invention contemplates the preparation of a composition of matter comprising a polynucleotide or polypeptide attracted to a hydrated polysaccharide through a triphenylmethyl ether group bonded to said polysaccharide.

A wide range of polysaccharides may be used in accordance with this invention and includes agarose, cellulose, dextran, glycogen, carragheenan, starch, and mixtures thereof. The polysaccharides may be used in any desired form such as beaded, powdered, granular, fibrous, etc. More specifically, the polysaccharides found useful for supports herein include beaded cross-linked agarose, cellulose, beaded cross-linked dextrans, glycogen, carragheenan, starch, or a mixture thereof. A much preferred support is agarose. Beaded agarose (2, 4 or 6% by weight) is a linear polysaccharide composed of alternating residues of beta-dextro-galactopyranose and 3,6 anhydro-alpha-laevo-galactopyranose subsequently cross-linked with a propanol derivative to provide greater stability.

The preparation of the triphenylmethyl ether or tritylated derivative of polysaccharide shall now be considered and described. A polysaccharide such as agarose in beaded form is used in an aqueous suspension and is made anhydrous by filtering with ethanol and pyridine and thereafter azeotropically evaporating excess solvent to form an anhydrous suspension. To the anhydrous suspension is added a predetermined amount of trityl chloride, whereby the reagent reacts preferentially with the primary hydroxyl groups of the polysaccharide. In general, between about 1–2 g trityl chloride added to 20 ml of the suspension (containing 10 ml bed volume agarose) gives a "low" tritylated polysaccharide ($\leftarrow$15 $\mu$M trityl/ml) after about 45 minutes, a "medium" tritylated polysaccharide (15–40 $\mu$M trityl/ml) after 2 to 4 hours, and a "high" tritylated polysaccharide ($\leftarrow$40 $\mu$M trityl/ml) after 12–20 hours reaction at room temperature. An alternative mode of synthesis may be used, the synthesis being more convenient because it affords higher yields, proceeds more quickly, and avoids the use of the noxious pyridine. For example, a 10 ml bed volume of an aqueous agarose suspension is washed with ethanol and dimethyl formamide (DMF) and then evaporated in the presence of excess DMF until an anhydrous suspension is obtained. To this suspension is added: 9.6 mg p-dimethyl amino pyridine, 614 mg trityl chloride, and 300 $\mu$l of triethylamine.

"Low" trityl agarose is obtained within about 5-10 minutes, "medium" trityl agarose in 20-40 minutes and "high" trityl agarose in 1-2 hours, reaction time at room temperature.

In order for these tritylated polysaccharides to be effective in immobilizing polypeptides and polynucleotides, they must be in a hydrated form. The hydration may be achieved by first washing the newly tritylated polysaccharide with excess ethanol/DMF to remove unreacted trityl chloride and thereafter treating the suspension with water. In immobilizing polypeptides and polynucleotides according to the process of the subject invention, the physical denaturation or loss of activity of these macromolecules is exceedingly low, since the immobilization reaction is carried out in an aqueous buffered phase under very mild conditions. Some indication of the general degree of tritylation may be made by visual observation of the hydrated polysaccharide as held up to a light source, in that those compositions having a low degree of tritylation are generally clear, whereas those compositions having a high degree of tritylation are milky-white and opaque. The preferred amount of hydration for the tritylated polysaccharides may vary over a wide range. However, at least about 60% water for the tritylated polysaccharide has been found advantageous. Another preferred amount of hydration is about 80%, and yet a more preferred range is between about 95 to 96% hydration. In these active forms, the compositions are, in effect, hydrated gels.

Polypeptides that may be immobilized in accordance with this invention include enzymes, serum proteins such as albumin and immunoglobulins and hormonal proteins. The enzymes which may be immobilized include purified as well as crude enzymes, enzyme mixtures, and enzyme systems present in or isolated from animal, plant, or microbial tissue. Proteolytic enzymes, such as trypsin, chymotrypsin, carboxypeptidase A, proteinase K, and papain; hydrolases such as alpha amylase, invertase, betagalactosidase, ribonuclease, ATPase, alkaline and acid phosphatases, amyloglucosidase, and dextranase; dehydrogenases such as pyruvate dehydrogenase; kinases such as creatine phosphokinase; oxidases such as glucose oxidase and amidases such as penicillin amidase may be used. A particular enzyme class which exhibits good activity are the so-called restriction endonucleases as well as the nucleotide bond synthesizing enzymes including polynucleotide phosphorylase (*M. luteus*), DNA polymerase I (*E. coli*), RNA polymerase (*E. coli*), RNA ligase, polynucleotide kinase, AMV reverse transcriptase and phosphoglyceric acid kinase.

Further, it is contemplated that complex polypetides, such as interferon and the like, may be immobilized.

Polynucleotides that may be immobilized according to this invention include ribonucleic acids (RNA) such as poly A+mRNA, specific types of messenger RNA, whether or not they contain poly A sequences, such as fibroin mRNA, as well as ribosomal RNA, transfer RNA and viral RNA and deoxyribonucleic acids (DNA) especially where the DNA involves denatured DNA.

The affinity characteristics including binding efficiency and specificity may be controlled by the degree of tritylation, type of polysaccharide used and its form, degree of hydration, type of salt, etc.

The following non-limiting examples more particularly illustrate the present invention;

EXAMPLE 1

Preparation of Tritylated Agarose

A 10 ml bed volume of 4% beaded agarose (CL-4B) was washed with excess ethanol and dimethylformamide until anhydrous; to this suspension was added 10 ml of dimethylformamide, dried over type 4A molecular sieve beads, containing 614 mg of trityl chloride (2.0 equivalents relative to primary hydroxyl groups in the agarose), 9.6 mg (0.073 equivalents) of p-dimethylamino pyridine and 300 $\mu$l of triethylamine (2.73 equivalents). The latter 10 ml solution had been pre-equilibrated to 40° C.; the subsequent reaction likewise was done at 40°. At designated times, aliquots were withdrawn, washed with excess ethanol/DMF to remove non-covalently bound trityl groups, and the number of $\mu$Moles trityl incorporated/ml of packed volume determined as has already been described (Cashion et al., Nucleic Acids Research 8, pp. 1167-1185, 1980). Table I shows the agarose tritylation kinetics.

TABLE I

| Time | $\mu$ Moles trityl incorporated/ 1 ml bed volume agarose |
|---|---|
| ½ hour | 27 |
| 1 hour | 39 |
| 3 hours | 119 |
| 6 hours | 165 |

The tritylation of cellulose may be done analogously.

The following operational definitions have been assigned to tritylated agarose or tritylated cellulose: "low," "medium," and "high" refer to tritylated polysaccharides containing <15 $\mu$M Tr/ml, 15-40 $\mu$M Tr/ml, and >40 $\mu$M Tr/ml. The trityl ether linkage is stable indefinitely at room temperature under aqueous conditions; care should be taken, however, to prevent microbial growth in these polysaccharide columns by adding, for example, sodium azide or a similar antimetabolite.

EXAMPLE 2

Isolation of Poly A on Medium Trityl Agarose

A solution, 5 ml, containing 5 $A_{260}$ units (~250 $\mu$g) of poly A in a high salt buffer of 0.5 M NACl/0.05 M trihydroxy methyl aminomethane (Tris).HCl pH 7.5 (hereafter referred to as "HS"), was applied to a medium trityl agarose column (3 ml bed volume, 33 $\mu$M trityl/ml, inner diameter of plastic column 0.9 cm) which was equilibrated with 0.5 M NaCl/0.05 M Tris.HCl pH 7.5 high salt buffer (HS). Fractions of 2-3 ml were collected and their $A_{260}$ checked. After applying the 5 ml of poly A solution, and washing with a further 10-15 ml of HS solution to confirm that the poly A was bound, the column was next eluted with a low salt buffer of 0.05 M trihydroxy methylamino methane (Tris).HCl pH 7.5 (hereafter referred to as "LS"). The bound poly A was rapidly eluted by this LS solution; recovery of poly A in the LS wash was quantitative. As indicated in Table II, under these conditions, medium trityl agarose is absolutely specific for poly A relative to the other ribohomopolynucleotides.

TABLE II

| Polynucleotide | % Bound to Trityl Agarose |
|---|---|
| poly A | 100% |
| poly U | 0% |
| poly G | 0% |

TABLE II-continued

| Polynucleotide | % Bound to Trityl Agarose |
|---|---|
| poly C | 0% |

EXAMPLE 3

Isolation of Poly A+mRNA on Medium Trityl Agarose

About 40 $A_{260}$ units of natural RNA extracted by the hot phenol method from rabbit liver and dissolved in HS solution was applied to a medium (33 μM Tr/ml) of trityl agarose column (3 ml bed volume) equilibrated with HS. After washing the column with HS solution until the $A_{260}$ of the eluant was less than 0.05, the column was washed with LS solution (or alternatively with LS containing 0.1% w/w of sodium dodecyl sulfate). The latter fractions contained ~2 $A_{260}$ units (~5% of the total absorbance) of poly A+mRNA. The identity of the latter was established by running comparison columns with the established affinity column-dT cellulose. Likewise in this regard, a synthetic ribopolynucleotide, 3'-poly A terminated-5'-poly C, which simulates poly A+mRNA, was constructed and tested (Cashion et al., Nucleic Acids Research 8, pp. 1167-1185, 1980). It behaved identically to poly A+mRNA on both trityl agarose and dT cellulose.

EXAMPLE 4

Isolation of Denatured DNA on Trityl Agarose

An aqueous solution (~1 ml) of native DNA (5 $A_{260}$ units) was heat denatured by placing in boiling water for 5 minutes, quick cooling to room temperature, and diluting to 5 ml to give a HS solution. This solution was applied to a medium (33 μM Tr/ml) trityl agarose column (3 ml bed volume) equilibrated with HS and washed with HS until the eluant $A_{260}$ was less than 0.05 units. Next an LS solution was added (~15 ml), followed by a 4 M urea solution (~20 ml). Approximately half of the eluted DNA was found in the LS fraction and half in the urea fraction. Recovery was ~80%. Control columns using native duplex DNA showed no binding. Comparison columns run with nitro cellulose resins show identical specificity between the two, i.e., both bind single stranded denatured DNA at HS and release it in LS/urea-native DNA.

EXAMPLE 5

Immobilization and Stabilization of Enzymes on Medium to High Trityl Agarose

In general, in order to successfully immobilize and use any given enzyme on a trityl agarose column, one merely applies the buffered salt solution containing the enzyme to the trityl agarose column. This is followed by a number of washes of the column with the same buffered salt solution and then assaying the eluant for non-adsorbed enzyme. One then assays the trityl agarose-immobilized enzyme directly by allowing the appropriate buffered substrate solution, whose volume is equal to that of the column's bed volume, to adsorb into the column. The incubation is then carried out at the appropriate temperature for a given time and is terminated simply by washing the column with an excess of buffered salt solution (minus substrate); subsequently, the product may be assayed in the eluate and yields determined. The enzyme immobilized to trityl agarose is now stored at 5° C. until reuse. The following details the immobilization of bacterial (*E. coli*) alkaline phosphatase (bap) to trityl agarose: 20 units of bap in 200 μl of 0.1 M Tris.HCl pH 8 were applied to a medium (33 μM Tr/ml) trityl agarose column (1 ml bed volume) equilibrated with 0.1 M Tris pH 8. After adsorbing the enzyme and washing with ~6 bed volumes of buffer, it was determined that no enzyme activity was detectable in any of the wash fractions. The enzyme assay solution consisted of 10 mM p-$NO_2$ phenyl $Po_4$ in 0.1 M Tris, pH 8; the absorbance of the yellow $NO_2$-phenolate ion was measured at 410 nm. The trityl agarose-immobilized bap was next assayed directly by adsorbing a 1 ml volume of the assay solution into the column, leaving it for 45 minutes at room temperature and then eluting the products with buffer solution and determining the enzyme activity. In this case, trityl agarose-adsorbed bap had 100% of the activity of a control incubation done identically except that the enzyme was in free solution as opposed to a solid matrix. It has been found that this particular enzyme, and also the alkaline phosphatase isolated from bovine small intestine, is extremely stable when stored with 10 mM $ZnCl_2$ at a pH (Tris buffer) between 7 and 8 at 5° C. Under these conditions, both enzymes have catalytic half-lives in excess of 6 months. In general, it has been found that both the capacity for enzyme binding and the long-term stability of the bound enzymes increase with increasing trityl content, 100–150 μM trityl/ml being the best range. Table III is a list of the enzymes tested amd the efficiency of their immobilization in terms of the preservation of enzyme activity within the column.

TABLE III

ACTIVITY OF ENZYMES IMMOBILIZED ON TRITYL AGAROSE COLUMNS

|  | % Activity[a] |
|---|---|
| A. NUCLEASES | |
| 1. Alkaline Phosphatase (calf intestine) | 83 |
| 2. Alkaline Phosphatase (*E. coli*) | 100 |
| 3. Acid Phosphatase (wheat germ) | 61 |
| 4. Pancreatic DNase | 17 |
| 5. Venom Phosphodiesterase (*Crotalus ademanteus*) | 70 |
| 6. Micrococcal Nuclease | 100 |
| 7. ATPase | 42 |
| 8. $S_1$ Nuclease | ~80 |
| B. PROTEASES | |
| 1. Trypsin | 87 |
| 2. Chymotrypsin | <5[b] |
| 3. Carboxypeptidase A | <5[b] |
| C. NUCLEOTIDE BOND SYNTHESIZING ENZYMES | |
| 1. Polynucleotide Phosphorylase (*M. luteus*) | 73 |
| 2. DNA Polymerase I (*E. coli*) | 2 |
| 3. RNA Polymerase (*E. coli*) | 30 |
| 4. RNA Ligase ($T_4$) | 74 |
| 5. Polynucleotide Kinase ($T_4$) | 359[c] |
| 6. AMV Reverse Transcriptase | 13 |
| 7. $32_p$ ATP Preparation using glyceraldehyde-3-$PO_4$ dehydrogenase and 3-$PO_4$—glyceric acid kinase. | 83 |
| D. RESTRICTION ENDONUCLEASES | |
| 1. $EC_o$ RI | ~80 |
| 2. Hind III | ~80 |
| 3. Bam I | ~20 |

[a]Column-immobilized activity compared to similar assay in free solution. See Cashion et al., Nucleic Acids Research, Symposium Series No. 7, pp. 173–189, May 1980, for details.
[b]Given the specificity of these proteases for aromatic amino acids, it is hypothesized that the aromatic trityl groups themselves are inhibiting these enzymes.
[c]TA appears to stabilize the enzyme relative to free solution during a 60' assay.

Of the approximately 40 enzymes tested, only one, bovine pancreatic RNase, failed to bind to some degree; however, even this enzyme could be induced to bind by means of an alternative procedure (Cashion et al., Nucleic Acids Research 8, pp. 1167–1185, 1980).

EXAMPLE 6

Isolation of Specific Polynucleotides Using Tritylated Oligonucleotides as Complementary Ligands Two instances of this type of procedure are provided: one, a simple prototype reaction wherein tritylated oligothymidylic acid, anchored hydrophobically to low (13 $\mu$M trityl/ml) trityl agarose, serves as the ligand for the formation of complementary hydrogen bonds with poly A; a second reaction, wherein a synthetic tritylated deoxydodecanucleotide serves as a ligand to isolate fibroin essenger RNA.

In the first case, 8 $A_{260}$ units of 5' tritylated oligothymidylic acid (a 16-mer) in HS was applied to a low (13 $\mu$M Tr/ml) trityl agarose (2 ml bed volume, equilibrated with HS) column and washed with a few more bed volumes of HS. Having hydrophobically anchored this group to the column, 5.7 $A_{260}$ units of poly A in HS was applied and washed until the $A_{260}$ of the eluant was <0.05. Less than 5% of the applied poly A washed through the column in HS; upon washing the column with LS, the remaining 95% of the poly A was eluted. The tritylated oligo dT ligand remained bound to the column in LS; 50% ethanol served to elute it subsequently. A methodological variation on this experiment involves premixing the tritylated oligothymidylic acid and poly A in HS solution at room temperature, allowing hydrogen bonds to form and then subsequently passing the tritylated duplex through trityl agarose and finally eluting with LS as above.

In the second case, 8 $A_{260}$ units of a tritylated synthetic 12-mer, Tr(ACCAGC)$_2$, complementary in a hydrogen bonding sense to the fibroin mRNA, was added to a solution of fibroin mRNA (~2 $\mu$g; 5,000 CPM) which had been preheated for 4 minutes at 50° C. This latter mixture was quick cooled to 5°, made to HS and applied to a low (~15 $\mu$M TR/ml) trityl agarose column (2 ml bed volume, equilibrated with HS); ~20% of the mRNA failed to bind. Upon changing to LS, the remaining 80% of the fibroin mRNA which was bound at HS was eluted. Experiments done using differentially labeled rRNA as control showed no binding of the latter under conditions as described above (Cashion et al., Nucleic Acids Research 8, pp. 1167–1185, 1980).

EXAMPLE 7

Purification of Enzymes on Hydrophobic Trityl Agarose Columns

A crude (410 Kunitz units/mg) bovine pancreatic deoxyribonuclease sample (5 mg) in 2 ml of 2 M NaCl, 50 mM Tris.HCl pH 7.5 and 10 mM CaCl$_2$ was applied to a medium (33 $\mu$M trityl/ml) trityl agarose column (3 ml bed volume, equilibrated with the same salt solution at room temperature) and washed in with ~7 bed volumes of the buffer solution. Subsequently, the column was eluted with water (or water buffered with 5 mM Tris); the eluate fractions were checked for protein content by their $A_{280}$ and by the Lowry method. Activity assays for the enzyme involved increase in the $A_{260}$ of DNA substrate solutions. Most of the DNase activity was eluted in the water (or low salt) fractions, representing a purification or increase in the specific activity of the enzyme of about 5-fold.

Instead of using decreasing salt concentrations to elute an enzyme as above, increasing amounts of organic solvents such as n-propanol may also be used. A crude preparation of calf intestinal alkaline phosphatase (2 mg) dissolved in 1 ml of 0.1 M NH$_4$HCO$_3$, 1.9 M NaCl was applied to a low (18 $\mu$M Tr/ml) trityl agarose (10 ml bed volume) equilibrated with 0.1 M NH$_4$HCO$_3$, 1.9 M NaCl and washed in with 14 ml of the same solution. All of the enzyme activity was bound to the column, most of it localized at the very top. The column was next eluted with 12 ml volumes of 10%, 20%, and 30% isopropanol (the remaining volume percentages being water). The enzyme eluted in the 20% isopropanol fraction with a 3-fold increase in specific activity.

While the invention has been shown and described with reference to certain preferred embodiments thereof, those skilled in the art will appreciate that various changes, modifications, substitutions, and omissions can be generally made by those skilled in the art without departing from the spirit of the invention. It is intended, therefore, that the invention by limited only by the scope of the claims which follow.

What is claimed is:

1. A composition of matter, comprising a polynucleotide or polypeptide attracted to a substantially hydrated polysaccharide through a triphenylmethyl ether group bonded to said polysaccharide.

2. A composition of matter as recited in claim 1 wherein the polynucleotide is a ribonucleic acid.

3. A composition of matter as recited in claim 2 wherein the ribonucleic acid is messenger RNA.

4. A composition of matter as recited in claim 2 wherein the ribonucleic acid is ribosomal RNA.

5. A composition of matter as recited in claim 2 wherein the ribonucleic acid is transfer RNA.

6. A composition of matter as recited in claim 2 wherein the ribonucleic acid is viral RNA.

7. A composition of matter as recited in claim 1 wherein the polynucleotide is a deoxyribonucleic acid.

8. A composition of matter as recited in claim 7 wherein the deoxyribonucleic acid includes a denatured DNA.

9. A composition of matter comprising a poly A containing ribonucleic acid attracted to a substantially hydrated polysaccharide through a triphenylmethyl ether group bonded to said polysaccharide.

10. A composition of matter, comprising a polypeptide attracted to a substantially hydrated polysaccharide through a triphenylmethyl ether group bonded to said polysaccharide, said polysaccharide being hydrated at least about 60 percent by weight.

11. A composition of matter as recited in claim 10 wherein the polypeptide is an enzyme.

12. A composition of matter as recited in claim 11 wherein the enzyme is a nuclease.

13. A composition of matter as recited in claim 11 wherein the enzyme is a protease.

14. A composition of matter as recited in claim 11 wherein the enzyme is an endonuclease.

15. A composition of matter as recited in claim 11 wherein the enzyme is a member selected from the group consisting of polynucleotide phosphorylase, DNA polymerase, RNA polymerase, RNA ligase, polynucleotide kinase, AMV reverse transcriptase, and phospho glyceric acid kinase.

16. A composition of matter, comprising a polynucleotide or polypeptide attracted to a substantially hydrated polysaccharide through a triphenylmethyl ether group bonded to said polysaccharide, said polysaccharide being a member selected from the group consisting of agarose, cellulose, dextran, glycogen, carragheenan, starch, or a mixture thereof.

17. A composition of matter as recited in claim 16 wherein the hydrated polysaccharide contains at least about 60% water by weight.

18. A composition of matter as recited in claim 16 wherein the hydrated polysaccharide contains at least about 80% water by weight.

19. A composition of matter as recited in claim 16 wherein the hydrated polysaccharide contains at least about 95% water by weight.

20. A process for the immobilization of a polynucleotide or polypeptide, comprising forming a reaction product of triphenylmethyl ether of polysaccharide, hydrating substantially said reaction product, and reacting said hydrated reaction product with said polynucleotide or polypeptide to produce an immobilized composition of matter thereof.

21. A process of claim 20 wherein the polynucleotide is a ribonucleic acid.

22. A process of claim 21 wherein the ribonucleic acid is messenger RNA.

23. A process of claim 21 wherein the ribonucleic acid is ribosomal RNA.

24. A process of claim 21 wherein the ribonucleic acid is a transfer RNA.

25. A process of claim 21 wherein the ribonucleic acid is a viral RNA.

26. A process as recited in claim 20 wherein the polynucleotide is a deoxyribonucleic acid.

27. A process as recited in claim 26 wherein the deoxyribonucleic acid includes a denatured DNA.

28. A process for the immobilization of a poly A containing ribonucleic acid, comprising forming a reaction product of triphenylmethyl ether of polysaccharide, hydrating substantially said reaction product, and reacting said hydrated reaction product with a poly A containing ribonucleic acid to immobilize said acid.

29. A process for immobilizing a polypeptide, comprising forming a reaction product of triphenylmethyl ether of polysaccharide, hydrating substantially said reaction product, and reacting said hydrated reaction product with polypeptide to immobilize the same.

30. A process of claim 29 wherein the polypeptide is an enzyme.

31. A process of claim 30 wherein the enzyme is a nuclease.

32. A process of claim 30 wherein the enzyme is a protease.

33. A process of claim 30 wherein the enzyme is an endonuclease.

34. A process of claim 29 wherein the polypeptide is interferon.

35. A process as recited in claim 29 wherein the polypeptide is an enzyme selected from the group consisting of polynucleotide phosphorylase, DNA polymerase, RNA polymerase, RNA ligase, polynucleotide kinase, AMV reverse transcriptase, and phospho glyceric acid kinase.

36. A process for immobilization of a polynucleotide or polypeptide, comprising forming a reaction product of triphenylmethyl ether of polysaccharide, said polysaccharide being a member selected from the group consisting of agarose, cellulose, dextran, glycogen, carragheenan, starch, or a mixture thereof, hydrating substantially said reaction product, reacting said product with a polynucleotide or polypeptide to produce an immobilized composition of matter thereof.

37. A process of isolating a polynucleotide or polypeptide, comprising contacting a composition including said polynucleotide or polypeptide with a substantially hydrated gel of triphenylmethyl ether of a polysaccharide.

38. A process of claim 37 wherein the polysaccharide is agarose and the hydrated gel of triphenylmethyl ether of agarose contains at least about 60 weight percent water.

39. A process of claim 37 wherein the triphenylmethyl ether of the polysaccharide is hydrated at least about 80 weight percent.

40. A process of claim 37 wherein the triphenylmethyl ether of the polysaccharide is hydrated at least about 95 weight percent.

* * * * *